US00PP19280P2

(12) United States Plant Patent
Brown

(10) Patent No.: US PP19,280 P2
(45) Date of Patent: Oct. 7, 2008

(54) ***FUCHSIA* PLANT NAMED 'NUIFU 1'**

(50) Latin Name: *Fuchsia×hybrida*
Varietal Denomination: NUFU 1

(75) Inventor: Graham Noel Brown, Pennant Hills (AU)

(73) Assignee: NuFlora International of Macquarie Fields, NSW (AU)

( * ) Notice: Subject to any disclaimer, the term of this patent is extended or adjusted under 35 U.S.C. 154(b) by 0 days.

(21) Appl. No.: 11/804,332

(22) Filed: May 17, 2007

(51) Int. Cl.
*A01H 5/00* (2006.01)

(52) U.S. Cl. ..... Plt./300
(58) Field of Classification Search ..... Plt./300
See application file for complete search history.

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of *Fuchsia* plant named 'NUFU 1', characterized by its compact, upright to outwardly arching growth habit; freely branching plant habit; red purple and violet bi-colored flowers; freely and continuous flowering habit; and tolerance to low and high temperatures.

1 Drawing Sheet

Botanical designation: *Fuchsia×hybrida.*
Cultivar denomination: 'NUFU 1'.

BACKGROUND OF THE INVENTION

The present invention relates to a new and distinct cultivar of *Fuchsia,* botanically known as *Fuchsia×hybrida* and hereinafter referred to by the name 'NUFU 1'.

The new *Fuchsia* is a product of a planned breeding program conducted by the Inventor in Macquarie Fields, New South Wales, Australia. The objective of the breeding program is to create new compact and early-flowering *Fuchsia* cultivars that tolerate high and low temperatures.

The new *Fuchsia* originated from a cross-pollination made by the Inventor in November, 2000 in Macquarie Fields, New South Wales, Australia of a proprietary selection of *Fuchsia×hybrida* identified as code number X00.11.1, not patented, as the female, or seed, parent with a proprietary selection of *Fuchsia×hybrida* identified as code number X00.11.2, not patented, as the male, or pollen, parent. The new *Fuchsia* was discovered and selected by the Inventor as a single flowering plant within the progeny of the stated cross-pollination in a controlled greenhouse environment in Macquarie Fields, New South Wales, Australia in October, 2001.

Asexual reproduction of the new *Fuchsia* by terminal cuttings in a controlled environment in Macquarie Fields, New South Wales, Australia since October, 2001, has shown that the unique features of this new *Fuchsia* are stable and reproduced true to type in successive generations.

SUMMARY OF THE INVENTION

The cultivar NUFU 1 has not been observed under all possible environmental conditions. The phenotype may vary somewhat with variations in environment and cultural practices such as temperature, daylength and light intensity, without, however, any variance in genotype.

The following traits have been repeatedly observed and are determined to be the unique characteristics of 'NUFU 1'.

These characteristics in combination distinguish 'NUFU 1' as a new and distinct cultivar of *Fuchsia:*

1. Compact, upright to outwardly arching growth habit.
2. Freely branching plant habit.
3. Red purple and violet bi-colored flowers.
4. Freely and continuous flowering habit.
5. Tolerant to low and high temperatures.

Plants of the new *Fuchsia* differ primarily from plants of the parent selections in the following characteristics:

1. Plants of the new *Fuchsia* are more compact than plants of the parent selections.
2. Plants of the new *Fuchsia* flower earlier than plants of the parent selections.

Plants of the new *Fuchsia* can be compared to plants of the cultivar Kiecandiro, disclosed in U.S. Plant Pat. No. 15,410. In side-by-side comparisons conducted in Macquarie Fields, New South Wales, Australia, plants of the new *Fuchsia* and the cultivar Kiecandiro differed in the following characteristics:

1. Plants of the new *Fuchsia* were not as compact as plants of the cultivar Kiecandiro.
2. Plants of the new *Fuchsia* were not as upright as plants of the cultivar Kiecandiro.
3. Plants of the new *Fuchsia* had smaller flowers than plants of the cultivar Kiecandiro.

BRIEF DESCRIPTION OF THE PHOTOGRAPHS

The accompanying colored photographs illustrate the overall appearance of the new *Fuchsia,* showing the colors as true as it is reasonably possible to obtain in colored reproductions of this type. Colors in the photographs may differ slightly from the color values cited in the detailed botanical description which accurately describe the colors of the new *Fuchsia.*

The photograph at the bottom of the sheet comprises a side perspective view of a typical flowering plant of 'NUFU 1' grown in a container.

The photograph at the top of the sheet comprises a close-up of typical flowers of 'NUFU 1'.

DETAILED BOTANICAL DESCRIPTION

The aforementioned photographs and following observations, measurements and values describe plants grown in Encinitas, Calif., under commercial practice during the spring in a polyethylene-covered greenhouse with day temperatures averaged 24° C., night temperatures averaged 19° C. and light levels were about 4,000 foot-candles. Plants were grown for about 18 weeks in one-gallon containers and were pinched two times. In the following description, color references are made to The Royal Horticultural Society Colour Chart, 1995 Edition, except where general terms of ordinary dictionary significance are used.

Botanical classification: *Fuchsia×hybrida* cultivar NUFU 1.

Parentage:

*Female, or seed, parent.*—Proprietary selection of *Fuchsia×hybrida* identified as code number X00.11.1, not patented.

*Male, or pollen, parent.*—Proprietary selection of *Fuchsia×hybrida* identified as code number X00.11.2, not patented.

Propagation:

*Type.*—By terminal cuttings.

*Time to initiate roots, summer.*—About 21 days at temperatures of 20° C.

*Time to initiate roots, winter.*—About 23 days at temperatures of 18° C.

*Time to produce a rooted young plant, summer.*—About five weeks at temperatures of 18° C. to 20° C.

*Root description.*—Fibrous; white in color.

*Rooting habit.*—Freely branching; moderately dense.

Plant description:

*Plant and growth habit.*—Initially upright, then outwardly spreading; compact plant habit. Freely branching; about 22 lateral branches per plant. Moderately vigorous to vigorous growth habit.

*Plant height.*—About 25 cm.

*Plant diameter.*—About 38 cm.

Lateral branch description:

*Length.*—About 19 cm.

*Diameter.*—About 3 mm.

*Internode length.*—About 1.5 cm.

*Strength.*—Strong.

*Aspect.*—Initially upright to outwardly arching.

*Texture.*—Pubescent; minute hairs.

*Color.*—147C tinted with 182C.

Foliage description:

*Arrangement.*—Alternate, simple.

*Length.*—About 2.8 cm.

*Width.*—About 1.8 cm.

*Shape.*—Elliptic.

*Apex.*—Acute.

*Base.*—Attenuate.

*Margin.*—Entire with irregular minute points.

*Texture, upper and lower surfaces.*—Pubescent; minute hairs.

*Venation pattern.*—Pinnate; arcuate.

*Color.*—Developing foliage, upper surface: 137A. Developing foliage, lower surface: 147B. Fully expanded foliage, upper surface: 147A; venation, 147D. Fully expanded foliage, lower surface: 147B; venation, 147D.

*Petiole.*—Length: About 8 mm. Diameter: About 1 mm. Texture, upper and lower surfaces: Pubescent; minute hairs. Color, upper surface: 182C. Color, lower surface: 144C.

Flower description:

*Flower arrangement and habit.*—Single bi-colored axillary flowers. Flowers initially upright and then pendulous. Flowers not fragrant. Freely flowering habit with typically about 24 to 32 open flowers and flower buds per lateral branch.

*Natural flowering season.*—In southern California, plants flower from early spring to fall; flowering continuous during this period. Flowers last about seven to ten days on the plant. Flowers not persistent.

*Flower diameter.*—About 3.6 cm; corolla diameter, about 8 mm.

*Flower height.*—About 3.4 cm; corolla length, about 2.5 cm.

*Flower buds.*—Shape: Ovoid, elongate. Length: About 2.7 cm. Diameter: About 8 mm. Color: 54B.

*Petals.*—Arrangement: Four in a single whorl. Length: About 1.2 cm. Width: About 1.1 cm. Shape: Obovate to fan-shaped. Apex: Rounded. Margin: Entire. Texture, upper and lower surfaces: Smooth, glabrous; velvety. Color: When opening, upper surface: 77A. When opening, lower surface: 83A. Fully opened, upper surface: 83B; towards the base, 63C; color becoming closer to 72A with development. Fully opened, lower surface: 83A to 83B; towards the base, 87A.

*Sepals.*—Arrangement: Calyx star-shaped with four sepals fused at the base. Length: About 2 cm. Width: About 6 mm. Shape: Elliptic. Apex: Acuminate. Margin: Entire. Texture, upper and lower surfaces: Smooth, glabrous. Color: When opening and fully opened, upper surface: 63B. When opening and fully opened, lower surface: 63A.

*Peduncles.*—Length: About 1.3 cm. Diameter: About 1 mm. Angle: About 45° to 60° from vertical. Strength: Strong. Texture: Pubescent; minute hairs. Color: 145A.

*Reproductive organs.*—Stamens: Quantity: Eight per flower. Anther shape: Oblong. Anther size: About 1 mm by 2 mm. Anther color: 60B. Pollen amount: Scarce. Pollen color: 63A. Pistils: Quantity: One per flower. Pistil length: About 3.9 cm. Style length: About 3.3 cm. Style color: 61B. Stigma shape: Rounded. Stigma color: 77A. Ovary color: 146B. Seed/fruit: Seed and fruit development have not been observed on plants of the new *Fuchsia*.

Temperature tolerance: Plants of the new *Fuchsia* have been observed to tolerate temperatures from about 7° C. to about 32° C.

Pathogen/pest resistance: Plants of the new *Fuchsia* have not been observed to be resistant to pests and pathogens common to *Fuchsia*.

It is claimed:

1. A new and distinct *Fuchsia* plant named 'NUFU 1' as illustrated and described.

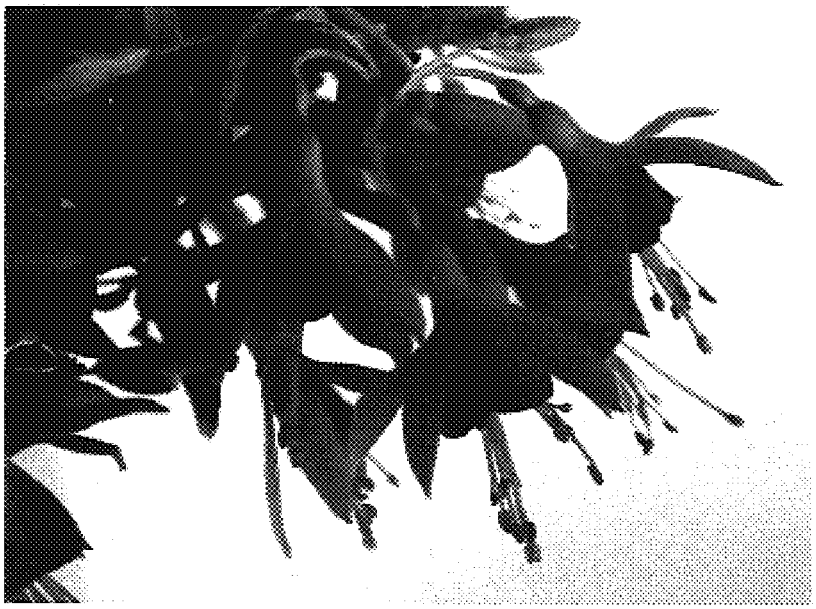
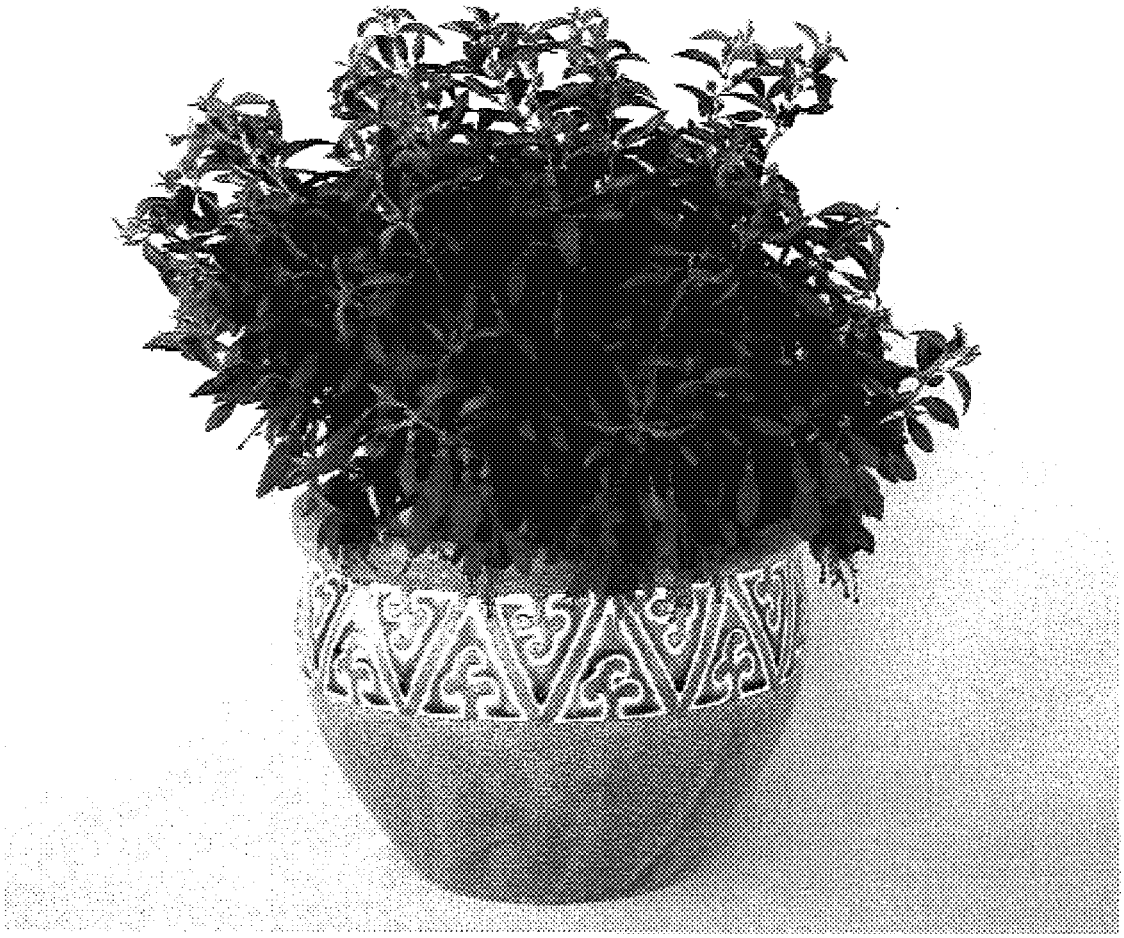

* * * * *